United States Patent [19]

Garman

[11] Patent Number: 5,857,852
[45] Date of Patent: Jan. 12, 1999

[54] ENDODONTIC FILE WITH NON-HELICAL FLUTES

[75] Inventor: Gary Garman, La Verne, Calif.

[73] Assignee: The Kerr Corporation, Orange, Calif.

[21] Appl. No.: 974,354

[22] Filed: Nov. 19, 1997

[51] Int. Cl.[6] .................................................. A61C 5/02
[52] U.S. Cl. ............................................................ 433/102
[58] Field of Search ..................... 433/81, 102, 141–143, 433/165, 166, 224

[56] References Cited

U.S. PATENT DOCUMENTS

| | | | |
|---|---|---|---|
| 322,265 | 7/1885 | Donaldson | 433/102 |
| 1,694,857 | 12/1928 | Kulik | 433/102 |
| 1,840,484 | 1/1932 | Brown | 433/143 |
| 4,019,254 | 4/1977 | Malmin | 433/102 |
| 4,231,738 | 11/1980 | Riitano et al. | 433/102 |
| 4,353,698 | 10/1982 | McSpadden | 433/81 |
| 4,836,780 | 6/1989 | Buchanan | 433/102 |
| 5,104,321 | 4/1992 | Filhol | 433/224 |
| 5,236,357 | 8/1993 | Randin | 433/102 |
| 5,350,298 | 9/1994 | Delaire | 433/102 |

FOREIGN PATENT DOCUMENTS

| | | | |
|---|---|---|---|
| 236232 | 9/1987 | European Pat. Off. | 433/143 |
| 3620527 | 12/1987 | Germany | 433/102 |
| 670756 | 7/1989 | Switzerland | 433/102 |
| 1271501 | 11/1986 | U.S.S.R. | 433/102 |

*Primary Examiner*—Ralph A. Lewis
*Attorney, Agent, or Firm*—Wood, Herron & Evans, L.L.P.

[57] ABSTRACT

An endodontic root canal file having an inner tapered core and a plurality of cutting sections lying between the core and an outer tapered envelope, each progressively decreasing in size from the proximate end to the distal end of the file. Each cutting section of the file having an intermediate cylindrical section extending radially outwardly from the core, a frusto-conical distal section tapering inwardly from the cylindrical section to the core and a planar annular proximate end surface section extending radially inwardly from the proximate end of the intermediate cylindrical section portion to the distal end of the next proximally adjacent cutting section. A plurality of grooves extend longitudinally and radially inwardly through the distal, intermediate and proximal sections of each cutting section and define non-helical flutes which provide distally and radially inwardly inclined cutting edges that lie in planes through the axis of the file and perpendicular to the circular circumference of the file. As a result, the torsional and bending axes of the file substantially coincide with the neutral axis thereof. The annular surface sections define shoulders having radially outer peripheral cutting edges that provide additional cutting action when the file reciprocates axially and aids in the removal of root canal material when the file is withdrawn from the root canal.

14 Claims, 3 Drawing Sheets

ENDODONTIC FILE WITH NON-HELICAL FLUTES

This invention relates to endodontic files, such as those used for root canals, and, more particularly, to flexible, tapered endodontic shaping files of the type used to clean, enlarge or shape deep narrow canals in tooth roots by continuous or oscillating rotational motion alone or in combination with reciprocating axial motion.

BACKGROUND OF THE INVENTION

Endodontic root canal files are small files held in the fingers of the dentist or endodontist to clean out decayed and damaged material from the root canal of a tooth and to shape the canal so that the root canal can be filled and the tooth can be restored. Typically, the root canal files are tapered, often helically fluted, and provided in sets of files of progressively increasing diameter. In use, the files are inserted into the root canal of the diseased tooth and are rotated, either continuously in one direction or by oscillatory rotational motion. The files are also used by reciprocating them longitudinally. Such files are required to follow the root canal of the tooth, which is usually curved, to ream as well as remove material from the tooth, and to do so without breaking the file while it is inserted in the root canal and without removing portions of the tooth root that are advantageously retained, that is, without ledging or perforating the canal.

Examples of prior art files are disclosed in U.S. Pat. Nos. 4,299,571, 4,538,989, 4,934,934 and 5,106,298, the disclosures of which are each expressly incorporated by reference herein.

Endodontic root canal files of the prior art, particularly those having helical flutes, have a tendency to pull into or push out of the canal when rotated, or to develop twisting moments when reciprocated. This can result in bent or broken files and cause the endodontist difficulty in controlling the file and thereby enlarge the canal in an unintended direction. Such helical files have a naturally non-round cross-section, which presents a spiraling neutral axis whereby the bending and torsional axes are not collinear, resulting in unequal stress. Such files present a compromise between bending flexibility and torsional rigidity. Furthermore, when such prior art files are rotated while bent, they have a tendency to produce a whipping or snaking action, where the axis of rotation is not about the geometric axis of the instrument, thereby producing inconsistent results in the shapes and sizes among the prepared root canals. In addition, the files of the prior art perform in a manner that is a compromise between cutting efficiency and efficiency of material removal.

Accordingly, there remains a need to provide an endodontic file that overcomes or avoids the problems experienced with the root canal files of the prior art discussed above.

SUMMARY OF THE INVENTION

It is a primary objective of the present invention to provide a root canal file that will overcome the shortcomings of root canal files of the prior art. It is a particular objective of the present invention to provide an endodontic file that is easy to control, effectively reams the root canal of a tooth and efficiently removes material from the root canal.

It is a more particular objective of the present invention to provide an endodontic root canal file that avoids the tendency to pull into or push out of the canal when the file is rotated and which avoids development of a twisting moment when axially reciprocated. It is a further objective of the present invention to provide a file that has a common bending and torsional axis, which rotates about its geometric centerline and which rotates without whipping or snaking. It is a particular objective of the present invention to provide an endodontic root canal file that avoids permanent bending and breaking forces and is easy to control. It is a specific objective of the present invention to provide a file that is of a non-helical flute design, that furnishes a round cross-section, and which presents a neutral axis where the bending and torsional axes are collinear.

According to the principles of the present invention, there is provided an endodontic file of the type that is useful for root canal preparation which has non-helical flutes. Preferably, the file has an overall round cross-section everywhere along its length, and its bending and torsional neutral axes substantially coincide.

According to the preferred embodiment of the invention, the file is provided with a plurality of fluted sections, the distal sides of which are tapered inwardly in the distal direction to provide guidance of the instrument into the canal, with an abrupt radial shoulder on the proximal side of the flutes to provide a ledge for the removal of debris and a cutting edge for push and pull instrumentation. The depth of the cut between the shoulder and the narrow distal ends of the flutes increases the flexibility of the file. Lands on generally cylindrical extensions of the wide proximal ends of the fluted sections also aid in the guiding of the instrument in the canal while providing extended cutting edges to increase those provided by the axial grooves through the tapered sections. The longitudinal grooves that define the flutes are perpendicular to the cutting direction when the file is used in rotation, which provides high efficiency in shearing material from the canal walls. These longitudinal grooves form the cutting edges in intervening fillets that are the primary cutting structure when the instrument is used in a rotary motion. The grooves also provide a path for debris to exit the canal.

In the preferred embodiment of the invention, spacing between the axial grooves is such that, when rotated through 60 degrees (+/−30°), four cutting edges come into contact with any given point on the canal wall, everywhere except along a "safety side" where the grooves are spaced farther apart so that only two cutting edges come into contact with the wall of the canal, which halves the cutting action. This spacing is alternatively further increased or decreased to allow different cutting rates to occur on different sides of the file, which can allow one side of the canal to receive relatively little or no cutting action. This allows the practitioner to control the transverse direction of the cutting or reaming action.

The file of the preferred embodiment of the present invention can be used in either continuous or oscillatory rotation or in push and pull fashion, and produces equivalent cutting efficiency when rotated in either direction. When used in rotation, the file provides additional safety, particularly by avoiding a tendency to pull itself into or push out of the canal and by reducing the incidence of permanently bent or broken files and the production of unwanted or uncontrolled cutting at the dental site. The preferred embodiment of the invention produces an axial force that is restricted to that directly applied by the endodontist's hand, which is more easily controlled. Bending flexibility and torsional stiffness are both optimally maximized. The taper of the fluted sections is preferably symmetrical about the axis of the instrument, which aids in the guiding of the file into the canal and reduces the chances of ledging and perforation.

These and other objectives of the present invention will be readily apparent from the following detailed description of the present invention.

DETAILED DESCRIPTION OF THE PREFERRED EMBODIMENTS

Figure 1:
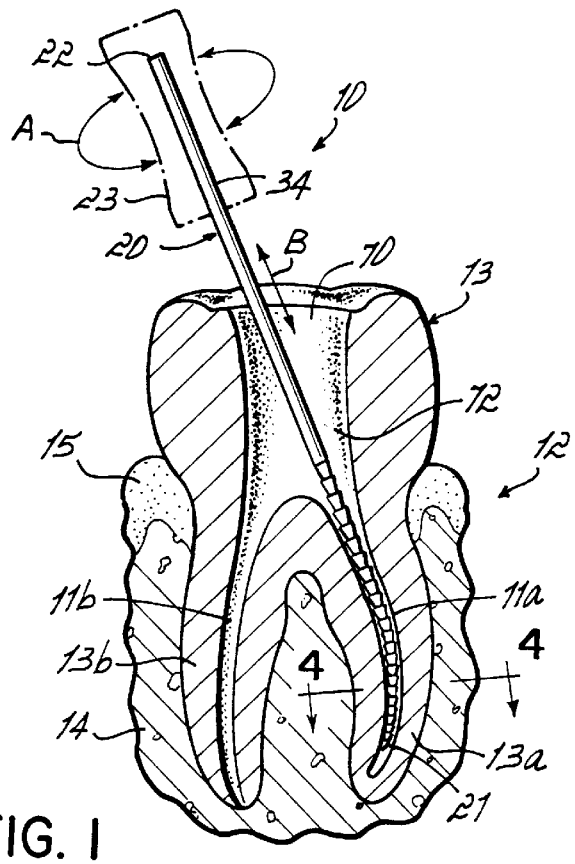
FIG. 1 is a schematic view, partially in perspective and partially in cross-section, of one preferred embodiment of a file embodying the principles of the present invention, illustrated in the process of cleaning the root canal of a tooth.

FIG. 1 illustrates a file 10 of one preferred embodiment of the present invention in the process of being used to remove the decayed interior of a tooth root canal 11$a$, illustrated as a lower molar, located in the lower jaw 12 of a dental patient, with canals 11$a$ and 11$b$ of tooth roots 13$a$ and 13$b$ of the tooth 13 shown in position in the bone 14 of the jaw 12, below the gum 15. The file 10 is formed of a slender one-piece shank 20 of a hard flexible material, such as a metal or other material having sufficient hardness to ream or cut the anatomical material surrounding root canal 11$a$ or 11$b$ of a tooth 13. The shank 20 is preferably formed of a high elasticity corrosion resistant metal, preferably a metal such as nickel titanium superelastic alloy, and has a gradual overall taper toward a smaller remote or distal free end 21 from a thicker proximate end 22. Fixed to the proximate end 22 is a small finger grip or handle 23, illustrated in phantom, by which the dentist can rotate the file 10, either by a continuous or oscillating rotational motion, and/or reciprocate it longitudinally or axially, as illustrated by arrows A and B, respectively.

Figure 3:
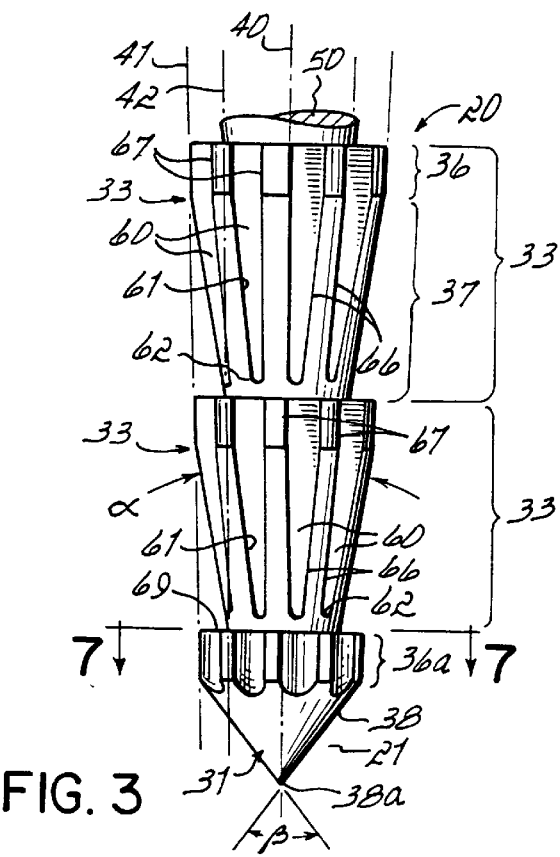
FIG. 3 is an enlarged side view of the tip of the file of FIG. 2.
Figure 2:
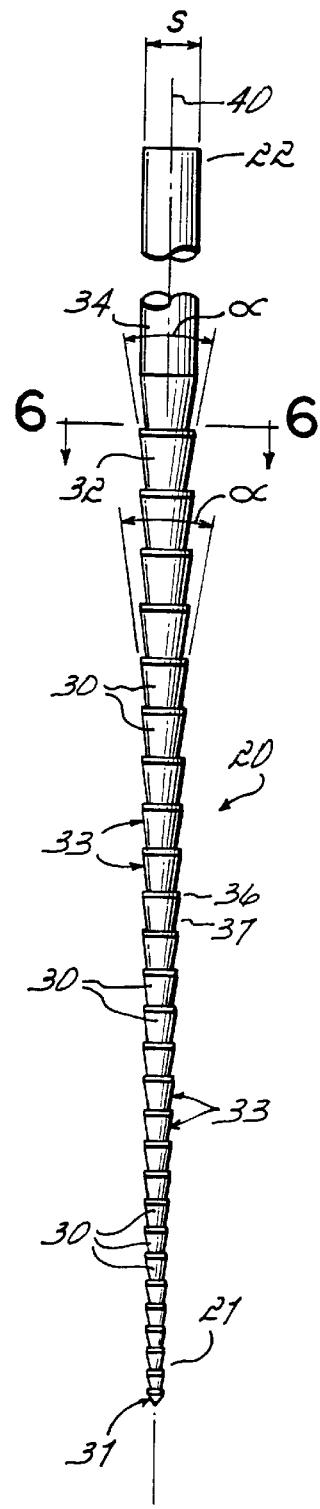
FIG. 2 is a schematic side view of the embodiment of the file of FIG. 1, in which the axial grooves of the various sections of the file have been eliminated from the drawing for simplicity.

As illustrated in FIG. 2, the shank 20 of the file 10 is formed, preferably machined, into a plurality of fluted sections 30, including a first fluted section 31 at the remote, distal or free end 21 of the shank 20, a last fluted section 32 spaced from the proximate end 22 of the shank 20 and a plurality of intermediate fluted sections 33 spaced between the first and last fluted sections 31 and 32. Adjacent the last fluted section 32 at the proximate end 22 of the shank 20 is a cylindrical stem 34 to which the handle 23 (FIG. 1) is bonded or otherwise fixedly mounted in any convenient manner. The stem 34 has a stem diameter S, which is the maximum diameter of the finished shank 20. The stem diameter S is typically about 0.041 inches. The shank 20 is defined by a central longitudinal axis or centerline 40, two generally frusto-conical surfaces, including an outer cone 41, which defines the overall taper of the file 10, and an inner cone 42, which defines a continuous inner core 50 of the file, as better illustrated in the enlarged view, FIG. 3.

Figure 6:
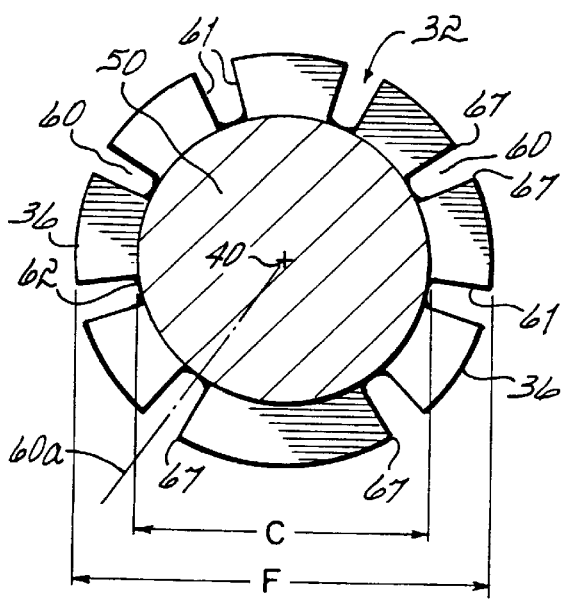
FIG. 6 is a cross-sectional view taken along the line 6—6 of FIG. 2.
Figure 7:
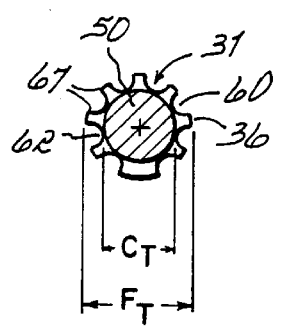
FIG. 7 is a cross-sectional view taken along the line 7—7 of FIG. 3.
Figure 8:
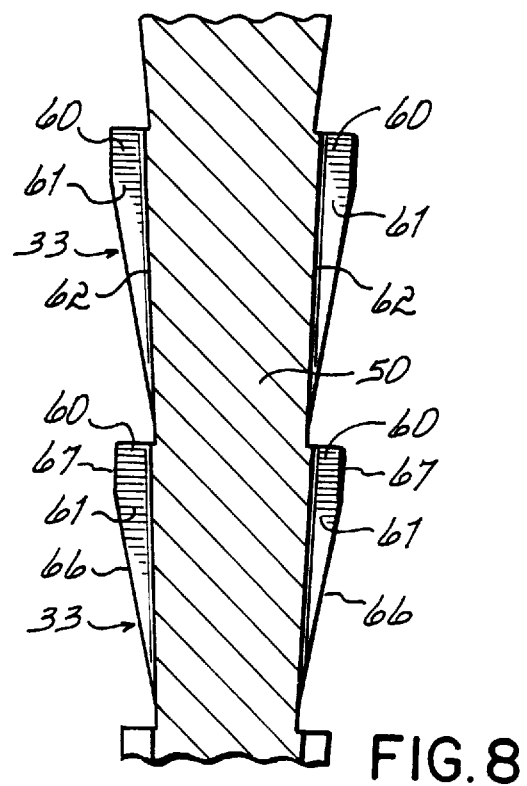
FIG. 8 is a cross-sectional view taken along the line 8—8 of FIG. 4.

As illustrated in FIGS. 6 and 7, the outer cone 41 defines a tapered outer or land diameter of the shank 20, while the inner cone 42 defines a tapered inner or core diameter of the shank 20. The outer cone 41 tapers inwardly from an outer diameter F at the proximate end of the last section 32, adjacent stem 34, at a taper of, for example, 0.04 inches per inch, to a flute tip diameter $F_T$ at the outer surface of the first section 31 at the remote end 21 of the shank 20. The inner cone 42 also tapers inwardly from a core diameter C, smaller than the outer diameter F, at the proximal end of the intermediate section 33 that is adjacent to the last section 32, at a taper of, for example, 0.028 inches per inch, to a core tip diameter $C_T$ at the proximal end of the first section 31 at the remote end 21 of the shank 20. The core diameter C is related to the outer diameter and the length of the last section 32 such that the inner cone 42 will intersect at the base of the last section 32 with a cone originating on the outer cone 41 and having the convergence angle α of, for example, 18°. The angle α defines a smooth outer frusto-conical surface of the last section 32.

The last section 32 and each of the intermediate sections 33 is defined by a large diameter approximately cylindrical and preferably shallowly tapered land portion 36 which has its radially outermost surfaces lying on the outer cone 41, and a smaller diameter more steeply tapered frusto-conical portion 37, located distally of the land portion 36 in each intermediate fluted section 33. The frusto-conical portions 37 each extend between the outer and inner cones 41 and 42 at the same taper angle α as of the last section 32. The land portions 36 and the larger proximal ends of the frusto-conical portions collectively define the overall taper of the outer cone 41, while the distal smaller ends of the frusto-conical portions 37 collectively define the inner cone 42. The land portion is typically 0.02 inches long when measured in a direction parallel to the centerline 40. As a result of these constraints, the lengths of the intermediate sections 33 progressively decrease from the proximal to the distal end of the file 10 since the lengths are determined by the intersections of inner and outer cones 41 and 42 with the cones of angle α that bounds the outer surfaces of the frusto-conical portions 37 of the fluted sections 32 and 33.

The first section 31 also has a land portion 36$a$ and a smooth conical portion 38 that is more steeply tapered than the angle α of the frusto-conical portions 37 of the fluted sections 32 and 33. The conical surface 38 converges to a point 38$a$ at an angle β, which is preferably about 75°. The first section 31, the intermediate sections 33 and the last section 32, constitutes the cutting sections of the file 10.

The inner cone 42 bounds a solid inner core 50 of the shank 20 which is of a circular cross-section throughout the length of the stem 20. Between the cones 41 and 42, the generally cylindrical or shallow tapered surfaces 36 and the frusto-conical surfaces 37 of last section 32 and each of the intermediate sections 33 and the cylindrical surface 36$a$ of the first section 31 are interrupted by a plurality of circumferentially spaced longitudinally oriented grooves 60. Each groove 60 has a plane of symmetry 60$a$, which is parallel to and contains the axis 40, as illustrated in FIG. 6. Each groove 60 has a semicircular groove bottom 62 which is located on or not more than 0.003 inches radially outward of the inner cone 41.

The strength of such a file 10 having the features set forth above is enhanced by the absence of helical flutes or other helical features. The flexibility of the file 10 is enhanced by the fact that the tapered sections present rings of the reduced diameter of the core or inner cone 42 that completely encircle the core 50 in planes perpendicular to the axis 40 of the shank 20 of the file 10.

Figure 4:
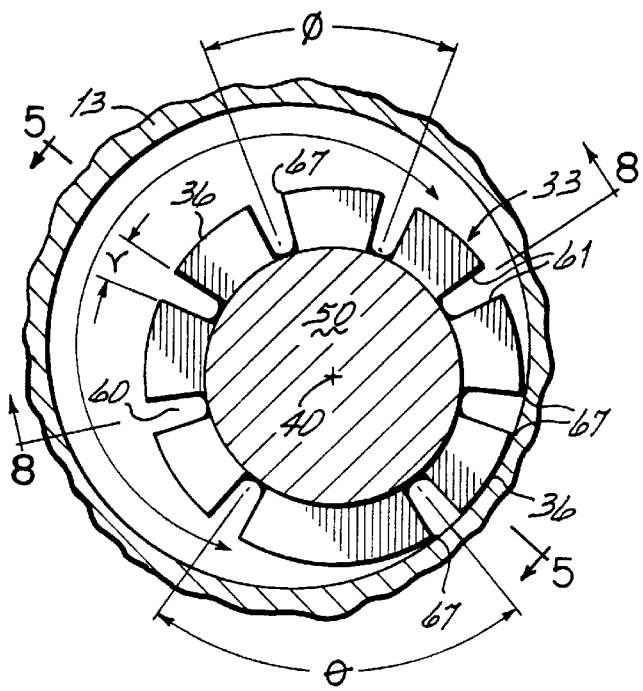
FIG. 4 is a cross-sectional view taken along the line 4—4 of FIG. 1.
Figure 5:
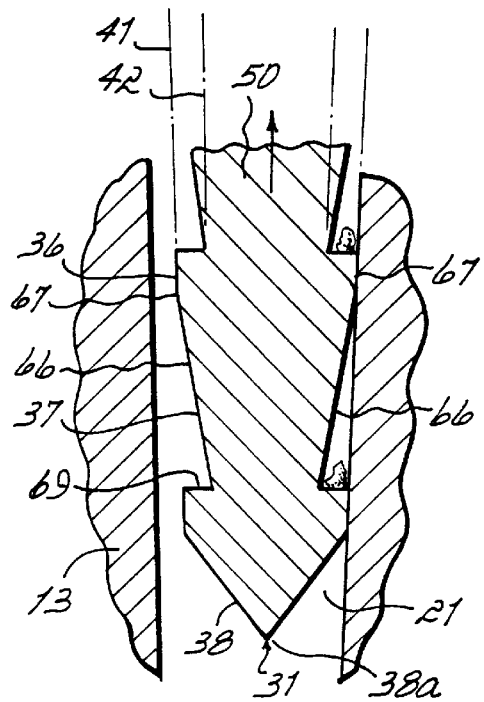
FIG. 5 is a cross-sectional view taken along the line 5—5 of FIG. 4.

The grooves 60 are illustrated in detail in the cross-sectional view of FIG. 4. The grooves 60 are, in the illustrated embodiment, eight in number and are identically shaped. Each has sides 61 that lie in planes through the axis 40 of the shank 20 that converge toward a concave semi-cylindrical groove bottom 62 of a radius, preferably of from about 0.0010 to 0.0015 inches. The grooves 60 are preferably of an included angle γ of about 10°. The grooves 60 are preferably spaced more closely on one side of the shank 20 than the other. For example, in the illustrated embodiment, seven of the center-to-center angular distances φ between adjacent grooves 60 are approximately 41° apart, while the remaining angular distance θ is approximately 73°. The outer edges of the grooves 60 at the outer surfaces of the land portions 36 and at the outer surfaces of the frusto-conical portions 37 of the fluted sections respectively form cutting edges 67 and 66 that perform the cutting function when the file 10 is rotated in a canal about the file axis 40. As a result differing center-to-center angular distances θ and φ, an oscillating rotation of the file through an arc of roughly 50° to 60° will bring up to four generally longitudinal cutting edges 67 and 66, respectively, of fluted frusto-conical portions 37 and land portions 36 moving perpendicularly across the inside surface of the root canal that is to be reamed (FIG. 5). On the other hand, the side of the root canal adjacent the side of the file 10 where the grooves 60 are spaced by the wider angle θ will have nominal contact by cutting edges 66 and 67. This facilitates control by the user of the direction of the reaming action in the root canal.

When reciprocated longitudinally in the root canal, the ledges 69, which are defined by upwardly facing annular planar surfaces that extend between the cones 41 and 42 at the bases of 18° tapers, serve as conveyors to remove debris from the root canal as the file 10 is drawn out of the upper extremity 70 of hole 72 in the crown of the tooth, as illustrated in FIG. 5.

The files 10 are preferably provided in a number of sizes having different numbers of cutting sections, lengths and diameters. Preferably, about ten sizes of files 10 are provided which range from the most slender and flexible file to a thickest and stiffest file. The most slender and flexible file has, for example, about thirty-seven cutting sections, a tip outer cone diameter $F_T$ of approximately 0.0061 inches, a tip core diameter $C_T$ of approximately 0.0043 inches, an outer cone diameter F of approximately 0.0349 inches, a core diameter C of approximately 0.0245 inches, a length of the tip section 32 of about 0.0059 inches and an overall length from the tip to the proximate end of the intermediate sections 33 of about 0.726 inches. The thickest and stiffest file has, for example, about twelve cutting sections, a tip outer cone diameter $F_T$ of approximately 0.0243 inches, a tip core diameter $C_T$ of approximately 0.0170 inches, an outer cone diameter F of approximately 0.0399 inches, a core diameter C of approximately 0.0279 inches, a tip section 32 length of about 0.0178 inches and an overall length from the tip to the proximate end of the intermediate sections 33 of about 0.407 inches. Intermediate sizes are provided with dimensions and quantities of cutting sections between these values. Preferably also, files are provided in differing lengths of the shank from the base of the handle 23 to the tip. For example, such sizes may be 21 mm, 25 mm and 30 mm.

Those skilled in the art will appreciate that the applications of the present invention herein are varied, and the invention is described in preferred embodiments. Accordingly, additions and modifications can be made to the embodiments of the invention illustrated and described herein without departing from the principles of the invention.

Therefore, what is claimed is:

1. An endodontic root canal file comprising:

a slender elongated shank having an outer surface, a central axis, a proximate end and a distal end;

the outer surface of the shank being formed of a plurality of axially aligned distally converging surface sections which decrease in size in the distal direction along the shank;

the distal ends of the distally converging surface sections encircling a tapered solid core which decreases in diameter from the proximate end to the distal end of the shank; and the distally converging surface sections having a plurality of angularly spaced grooves therein, each lying in a radially extending plane through the axis of the shank, thereby forming a plurality of angularly spaced non-helical flutes radially outward of the core.

2. The file of claim 1 wherein:

the surface of the shank includes a plurality of annular rings, each lying in a plane perpendicular to the central axis, and each having an inner edge connecting to the distal end of one of the distally converging surface sections and an outer edge connecting to the proximate end of the next distal one of the distally converging surface sections.

3. The file of claim 1 wherein:

the shank has a generally circular cross-section along its length.

4. The file of claim 1 wherein:

at least one pair of adjacent grooves is more widely spaced than other pairs of adjacent grooves in the shank.

5. The file of claim 1 wherein:

the file has a common bending and torsional axis, so that the file rotates about the central axis without whipping or snaking.

6. The file of claim 1 wherein:

the shank has bending and torsional axes and a neutral axis which is substantially spatially coincident with each of the bending and torsional axes.

7. An endodontic root canal file comprising:

a slender elongated shank of a hard and flexible cutting material having a formed of an alternating plurality of frusto-conical sections and annular planer shoulder surfaces, each decreasing in size in relation to its distal position on the shank, and each frusto-conical section having a wider one of its ends on the proximate side thereof;

the shank having a solid core of circular cross-section with a diameter that decreases in relation to its distal position on the shank; and the frusto-conical sections having a plurality of angularly spaced grooves, each centered on a radially extending plane through the axis of the shank and each extending to a depth not greater than the core, defining a plurality of angularly spaced non-helical axially oriented flutes in the frusto-conical sections.

8. The file of claim 7 wherein:

the shank has a generally circular cross-section along its length.

9. The file of claim 7 wherein:

the shank includes a plurality of land sections having approximately cylindrical outer surfaces, each land section lying between one of the annular shoulder surfaces and the proximate end of the frusto-conical section immediately distal thereto, with the grooves extending through the land sections to present cutting edges on the approximately cylindrical surfaces thereof on opposite sides of the grooves so that the cutting edges are perpendicular to the circumference of the file at the land sections.

10. An endodontic root canal file comprising:

a slender elongated shank of a hard and flexible cutting material having an outer surface, a central longitudinal axis, a distal end and a proximate end;

the shank having a solid inner core of gradually decreasing diameter in the distal direction;

the shank having a plurality of cutting edges lying on the outer surface and located radially outwardly of the core, the cutting edges being defined by grooves lying in radial-axial planes passing through and containing the axis and extending radially inwardly from the outer surface to not beyond the core, the cutting edges thereby being oriented longitudinally such that, when the shank is rotated about its axis, the cutting edges are disposed generally perpendicular to their direction of motion; and the shank being formed of a plurality of axially spaced substantially frusto-conical surface sections, each section having an inwardly tapering conical surface on the distal side thereof and an annular planar surfaces on the proximate side thereof, the sections decreasing in size in relation to their distal position on the shank, and the grooves extending through the inwardly tapering conical surfaces and through the annular planar surfaces.

11. The file of claim 10 wherein:

the shank further includes a plurality of approximately cylindrically-shaped land surface sections, each located between the proximate end of one of the cone-shaped surfaces and the outer edge of one of the annular planar surfaces, the grooves extending through the approximately cylindrically-shaped surfaces.

12. The file of claim 10 wherein:

the file that has a common bending and torsional axis, so that the file rotates about its geometric centerline without whipping or snaking.

13. The file of claim 10 wherein:

the shank has a neutral axis which is substantially spatially coincident with each of the bending and torsional axes.

14. An endodontic root canal file comprising:

a slender elongated shank of a hard and flexible cutting material having an outer surface, a central longitudinal axis, a distal end and a proximate end, the shank having:

a solid inner core of gradually decreasing diameter in the distal direction, and a plurality of cutting edges lying on the outer surface and located radially outwardly of the core, the cutting edges being defined by grooves lying in radial-axial planes passing through and containing the axis and extending radially inwardly from the outer surface to not beyond the core, the cutting edges thereby being oriented longitudinally such that, when the shank is rotated, about its axis the cutting edges are disposed generally perpendicular to their direction of motion;

a safety-side section between a pair of adjacent grooves spaced such that, when facing a given point on a root canal wall and the file is rotated through approximately 60°, only two cutting edges come into contact with the given point on the root canal wall; and a longitudinally directed opposite side section of increased cutting action wherein the axial grooves are spaced such that, when the opposite side section is facing the given point and the file is rotated through approximately 60°, four cutting edges come into contact with the given point on the root canal wall.

* * * * *

UNITED STATES PATENT AND TRADEMARK OFFICE
CERTIFICATE OF CORRECTION

| | | |
|---|---|---|
| PATENT NO. | : 5,857,852 | Page 1 of 1 |
| APPLICATION NO. | : 08/974354 | |
| DATED | : January 12, 1999 | |
| INVENTOR(S) | : Gary Garman | |

It is certified that error appears in the above-identified patent and that said Letters Patent is hereby corrected as shown below:

In claim 11, column 7, in lines 35 and 36, delete "cone-shaped surfaces", and insert therefor --frusto conical surface sections--, and, before "outer" change "the" to --a--.

In claim 12, column 8, line 3, delete "geometric centerline", and insert therefor --central longitudinal axis--.

In claim 13, column 8, line 6, after "has", insert --bending and torsional axes and--.

In claim 14, column 8, line 15, before "gradually", insert --a diameter--; after "decreasing", delete "diameter"; and at line 23, after "rotated", delete the comma; and at line 24, after "axis", insert a comma.

Signed and Sealed this

Twenty-fourth Day of July, 2007

JON W. DUDAS
*Director of the United States Patent and Trademark Office*